United States Patent
Maruyama et al.

(10) Patent No.: US 7,408,045 B2
(45) Date of Patent: Aug. 5, 2008

(54) ADSORBENT OF HIGH-MOBILITY-GROUP PROTEIN AND BODY FLUID-PURIFICATION COLUMN

(75) Inventors: Ikuro Maruyama, Kagoshima (JP); Nobuo Ida, Otsu (JP); Sanae Masuko, Kusatsu (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 11/490,095

(22) Filed: Jul. 21, 2006

(65) Prior Publication Data

US 2006/0258853 A1 Nov. 16, 2006

Related U.S. Application Data

(62) Division of application No. 09/980,624, filed as application No. PCT/JP01/02936 on Apr. 5, 2001, now abandoned.

(30) Foreign Application Priority Data

Apr. 5, 2000 (JP) ............................. 2000-103328

(51) Int. Cl.
*C07K 1/14* (2006.01)
(52) U.S. Cl. ................. 530/412; 530/415; 530/417; 604/5.01; 604/5.02; 604/5.03; 604/5.04
(58) Field of Classification Search ............... 530/412, 530/415, 417; 604/5.01, 5.02, 5.03, 5.04
See application file for complete search history.

(56) References Cited

U.S. PATENT DOCUMENTS

| | | | |
|---|---|---|---|
| 4,415,665 | A | 11/1983 | Mosbach et al. |
| 4,430,496 | A | 2/1984 | Abbott |
| 5,116,962 | A | 5/1992 | Stuber et al. |
| 5,773,605 | A | 6/1998 | Petitou et al. |
| 6,384,200 | B1 | 5/2002 | Wainwright et al. |
| 6,608,044 | B1 | 8/2003 | Aderka et al. |
| 6,774,102 | B1 | 8/2004 | Bell et al. |

FOREIGN PATENT DOCUMENTS

| | | |
|---|---|---|
| EP | 0 306 617 A2 | 3/1989 |
| EP | 0 321 703 | 6/1989 |
| EP | 0 616 845 A1 | 9/1994 |
| EP | 0 810 027 A1 | 12/1997 |
| EP | 1 057 529 A1 | 12/2000 |
| EP | 1 110 602 A1 | 6/2001 |
| WO | WO-91/04086 A1 | 4/1991 |

OTHER PUBLICATIONS

Jaber, B.L. (Am. J. of Kidney Disease 30(5) Suppl. 4:S44-S56, 1997).*
Reeves (Meth Enzymol. 304 155-188, 1999).*
Abdul Razzak (Preparative Biochemistry 17, 51-61, 1987).*
English Abstract of WO 01/18060, issued Mar. 2001.*
English Abstract of WO 00/66260, iisued Nov. 2000.*
Haichao Wang et al., *Science*, vol. 285, (Jul. 9, 1999), pp. 248-251.
Michael Ombrellino et al., *The Lancet*, vol. 354, (Oct. 23, 1999), pp. 1446-1447.
J. Sobajima et al., *Clin. Exp. Immunol.*, vol. 107, (1997), pp. 135-140.
Akihiko Taguchi et al., *Nature*, vol. 405, (May 18, 2000), pp. 354-360.
Osamu Hori et al., *The Journal of Biological Chemistry*, vol. 270, No. 43, (Oct. 27, 1995), pp. 25752-25761.
Garg LC; *Protein Expr. Purif.*; 14(2); Nov. 1998; pp. 155-159.
Isackson PJ; *Biochim Biophys Acta.*; Jun. 30, 1982; 697(3); pp. 378-380.
E. Rossomando, *Methods Enzymol.* (1990), 182 (Guide Protein Purif.) 309-17.
E. Karlsson, Protein Purification (2nd Edition) (1988), 145-205, Eds: Janson, Jan-Christer; Ryden, Lars. Publisher: Wiley-Liss, New York, NY.
J. Dennis, BioParm (Eugene, Oregon), vol. 11(4), pp. 44-48 & 50 (1998).

* cited by examiner

*Primary Examiner*—David Lukton
(74) *Attorney, Agent, or Firm*—Birch, Stewart, Kolasch & Birch, LLP

(57) ABSTRACT

An adsorbent of high-mobility-group proteins (HMG protein) which can remove HMG protein in body fluid is disclosed. The adsorbent according to the present invention has a water-insoluble carrier on which (a) substance(s) having (a) hydrogen-bondable functional group(s) and/or (a) hydrophobic functional group(s) is(are) immobilized.

22 Claims, No Drawings

ADSORBENT OF HIGH-MOBILITY-GROUP PROTEIN AND BODY FLUID-PURIFICATION COLUMN

CROSS-REFERENCE TO RELATED APPLICATIONS

The present application is a 37 C.F.R. § 1.53(b) divisional of U.S. application Ser. No. 09/980,624 filed Mar. 28, 2002, now abandoned, which claims priority on PCT International Application No. PCT/JP01/02936 filed Apr. 5, 2001, which claims priority on Japanese Patent Application No. 2000-103328 filed Apr. 5, 2000. Each of these applications is hereby incorporated by reference.

TECHNICAL FIELD

The present invention relates to an adsorbent for adsorbing high-mobility-group proteins (hereinafter also referred to as "HMG proteins" for short). The present invention is suitably used for improving the state of sepsis by removing HMG proteins in human blood.

BACKGROUND ART

HMG proteins are a group of non-histone DNA-binding proteins, and HMG-1, HMG-2, HMG14, HMG17, HMG-I (Y) and the like are known. HMG have been thought to participate in acceleration of transcription and growth of cells by binding to DNA in the cells. It was proved that amphoterin discovered as a factor which exists on the surface of nerve cells and extends dendrite is HMG-1 that is one of HMG proteins, so that it is suggested that HMG proteins exhibit a wide variety of actions.

Recently, it was reported that HMG-1 is secreted to the outside of the cells and acts as a strong mediator of systemic inflammation reaction and septic shock (Wang et al., (1999), Science, vol. 285, p. 248). That is, if lipopolysaccharide (LPS) is administered to a mouse, HMG-1 level in the serum is drastically increased at 8 to 24 hours after administration and the mouse dies. In case of administering purified HMG-1 together with LPS, these synergistically act and show lethal activity, and the lethal action by LPS is inhibited by administering an anti-HMG-1 antibody, so that it was shown that HMG-1 is an important mediator of endotoxin shock. In patients suffering from sepsis, HMG-1 level is drastically increased, especially where the patient dies. HMG-1 level in blood is also increased in hemorrhagic shock (Ombrellino et al., (1999), Lancet, vol. 354, p. 1446). Further, it has been reported that production of HMG-I(Y) belonging to HMG-1 is induced by stimulation with LPS.

It was observed that in autoimmune hepatitis, inflammatory bowel disease and in systemic rheumatic diseases, autoantibodies to HMG proteins such as HMG-1, HMG-2, HMG-14 and HMG-17 are produced, so that it is suggested that HMG proteins participate in these inflammatory diseases (Sobajima et al., (1997), Clin. Exp. Immunol., vol. 107, p. 135). Further, it has been reported that HMG proteins participate in growth of cancers (Taguchi et al., (2000), Nature, vol. 405, p. 354).

Thus, although HMG proteins have functions which are necessary to the body, in diseases such as sepsis, they are secreted in excess to the outside of the cells to make the disease worse and to make the body die. A candidate of the method for improving the state of the diseases caused by HMG proteins is to administer a drug such as an antibody, which binds to HMG and inhibits its action. However, in view of the fact that HMG proteins have functions which are necessary in the cells and on the surfaces of the cells, it is concerned that administration of a drug inhibiting HMG activity may cause serious side effects. Thus, it is desired to provide means for selectively removing extracellular HMG proteins which are undesirable to the body.

It has been reported that some substances such as heparin and RAGE, in addition to the above-mentioned antibodies, bind to HMG proteins (Hori et al., (1995), J. Biol. Chem. vol. 270, p 25752, and so on). However, it has not hitherto been proposed to use these HMG protein-binding substances for removing HMG proteins from the body, and no materials which can remove HMG proteins from body fluids are known.

DISCLOSURE OF THE INVENTION

Accordingly, an object of the present invention is to provide an adsorbent of HMG proteins which can effectively remove HMG proteins in body fluid.

The present inventors intensively studied to discover that by immobilizing a substance having a particular functional group, the HMG proteins in body fluid can be effectively removed, thereby completing the present invention.

That is, the present invention provides an adsorbent of high-mobility-group proteins comprising a water-insoluble carrier on which (a) substance(s) having (a) hydrogen-bondable functional group(s) and/or (a) hydrophobic functional group(s) is(are) immobilized. The present invention also provides a body fluid-purification column for removing high-mobility-group proteins, comprising a column, and the adsorbent according to the present invention. The present invention further provides a method for adsorbing high-mobility-group proteins in body fluid, comprising contacting the adsorbent according to the present invention with body fluid so as to adsorb the high-mobility-group proteins in the body fluid to the adsorbent. The present invention further provides a use of the adsorbent according to the present invention for production of adsorbent material for adsorbing high-mobility-group proteins in body fluid.

By contacting the adsorbent of the present invention with the body fluid, the HMG proteins in the body fluid are effectively adsorbed by the adsorbent so as to eliminate HMG proteins from the body fluid, so that the extracellular HMG proteins which are undesirable to the body may be removed.

BEST MODE FOR CARRYING OUT THE INVENTION

As described above, the adsorbent of HMG proteins according to the present invention comprises an adsorbent of high-mobility-group proteins comprising a water-insoluble carrier on which (a) substance(s) having (a) hydrogen-bondable functional group(s) and/or (a) hydrophobic functional group(s) is(are) immobilized.

Examples of the hydrogen-bondable functional group include cationic functional groups such as primary amino group, secondary amino group, tertiary amino group, imino group and quaternary ammonium group; anionic functional groups such as carboxyl group, sulfate groups, sulfonic acid group and phosphate group; and functional groups and structures having large polarity such as hydroxyl group, thiol group, aldehyde group, carbonyl group, urea bond and thiourea bond.

Among these, cationic functional groups and anionic functional groups are preferred.

Among the cationic functional groups, amino groups and quaternary ammonium group are especially preferred. Examples of the especially preferred amino groups and quaternary ammonium group include those represented by the following Formula (I):

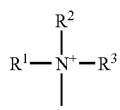

(wherein $R^1$, $R^2$ and $R^3$ independently represent hydrogen atom or a $C_1$-$C_5$ alkyl group, respectively)

It should be noted that in the present specification and in the claims, the term "alkyl group" includes both linear and branched alkyl groups.

Among the groups represented by Formula (I), those wherein $R^1$, $R^2$ and $R^3$ independently represent hydrogen atom or a $C_1$-$C_2$ alkyl group, respectively, are more preferred, and those wherein all of $R^1$, $R^2$ and $R^3$ represent methyl group are still more preferred. The functional groups may be employed individually or in combination.

As the anionic functional groups, among those described above, carboxyl group, sulfate groups and sulfonic acid group are especially preferred. These functional groups may be employed individually or in combination.

As the hydrophobic functional groups, alkyl groups having not less than 6 carbon atoms, and aromatic groups are preferred. Although there is no specific upper limit of the number of carbon atoms in the alkyl group, it is usually about 30. Examples of the aromatic groups include phenyl group, naphthyl group, and arylalkyl group and aralkyl group in which phenyl group or naphthyl group is substituted with one or more alkyl groups (preferably the number of carbon atoms in each alkyl group is 1 to 30). These functional groups may be employed individually or in combination.

The substance which is to be immobilized on the water-insoluble carrier is not restricted as long as the substance has one or more of the above-mentioned functional groups. Examples of the substance include low molecular synthetic compounds; synthetic polymers; naturally occurring low molecular compounds such as amino acids and sugars; saccharides such as oligo saccharides and polysaccharides, and derivatives thereof, peptides, proteins and modified products thereof; nucleic acids such as DNAs and RNAs, and derivatives thereof; and other physiologically active substances, biopolymers and compounds originated from microorganisms. In view of the stability to sterilization treatment, those having molecular weights of not more than 20,000 are preferred, and those having molecular weights of not more than 5000 are more preferred. Especially, those having molecular weights of about 50 to 500 are preferred.

Preferred examples of the above-mentioned substances having cationic functional groups include amino acids such as lysine and arginine, and peptides consisting of, or containing a large amount of (preferably not less than 30 mol %) these amino acids, for example, polylysine.

Examples of the substances having anionic functional groups include heparin and dextran sulfate which are sulfated polysaccharides containing a number of sulfate groups, as well as derivatives thereof. Since what is necessary is the sulfate group, the term "derivative" includes any derivatives which retain the sulfate groups of the heparin or dextran sulfate. Examples of the preferred substances having carboxyl group or sulfonic acid group include amino acids such as aspartic acid and glutamic acid, and peptides consisting of, or containing a large amount of (preferably not less than 30 mol %) these amino acids.

Preferred examples of the substances having hydrophobic functional groups include hydrophobic amino acids such as phenylalanine and tryptophan, and peptides consisting of, or containing a large amount of (preferably not less than 30 mol %) these amino acids.

Although the density of the above-mentioned functional groups is not restricted, the number of the above-mentioned functional groups (in cases where a plurality of kinds of functional groups are contained, the total thereof) per 1 g dry weight of the water-insoluble carrier on which the functional groups are immobilized is preferably about 1 μmol to 1 mmol, more preferably about 10 μmol to 1 mmol.

A material comprising a water-insoluble carrier and (an) antibody(ies) to HMG protein may also be used as the adsorbent of the HMG protein. Examples of the materials which may suitably be used as the water-insoluble carrier used in the present invention include synthetic polymers such as polyamides, polyimides, poly(aromatic vinyl compounds), polyesters, polymethylmethacrylates, polysulfones, polyethylenes, polyvinylalcohols and polytetrafluoroethylenes; and naturally occurring polymers such as cellulose, collagen, chitin, chitosan and dextran, as well as derivatives thereof. In addition, inorganic materials such as metals, ceramics and glass, of which surfaces are covered with an appropriate polymer, and of which surfaces are directly modified may also be suitably employed.

The material used in the present invention may be in the form of fibers, hollow fibers, beads, flat membrane, or powder. Those in the form of fibers, hollow fibers or beads, which are also suited for extracorporeal circulation of whole blood in which blood cells and plasma pass through a column without being separated, are preferred. To increase the rate of adsorption, porous materials having large contacting area are preferred. As the beads, since those giving small pressure loss when being packed in a column, and since those having large surface area are preferred, those having particle sizes of 50 to 1000 μm, especially 200 to 700 μm, are preferred.

The adsorbent according to the present invention may preferably be one which selectively adsorb HMG protein such that, when the above-mentioned adsorbent of the present invention is subjected to adsorption treatment of HGM-containing serum, the rate of adsorption of the HMG protein is not less than 50%, preferably not less than 80%, still more preferably not less than 90%, still more preferably not less than 95%, and the rate of adsorption of albumin in serum is not more than 20%, preferably not more than 15%, and still more preferably not more than 10%. Such an adsorbent which selectively adsorb HMG protein may be obtained by immobilizing the above-mentioned preferred functional groups on the water-insoluble carrier at the above-mentioned preferred density, and a plurality of concrete examples are described in the Examples below.

The term "rate of adsorption" of HMG protein or albumin means what percent of bovine HMG-1 protein in the sample solution is adsorbed, or what percent of serum albumin in the sample solution is adsorbed, when 50 μl of the adsorbent is added to 0.4 ml of sample solution prepared by adding bovine HMG-1 protein to normal human serum to a concentration of 600 ng/ml, and then shaking the resulting mixture at 37° C. for 2 hours.

Immobilization of the substance having the above-mentioned functional groups on the water-insoluble carrier via covalent bond may be accomplished by known methods such as reaction with the carrier activated with cyanogen bromide, polycondensation by carbodiimide, crosslinkage by a divalent reagent which reacts with amino group or thiol group, and crosslinkage by glutaraldehyde.

As is apparent from the above description, those wherein the substance containing the above-mentioned functional group(s) is bound to the water-insoluble carrier via covalent bond is also included in "water-insoluble carrier on which the substance is immobilized." Further, those wherein the above-mentioned functional groups are introduced or included from the step of synthesizing the water-insoluble carrier is also included in "water-insoluble carrier on which the substance is immobilized."

By packing the adsorbent according to the present invention in a column, a body fluid-purification column for removing high-mobility-group proteins is obtained. In cases where the adsorbent is in the form of fibers, the adsorbent may be packed into the column by making the fibers into woven fabric, knit or non-woven fabric, and by stacking and packing the resulting fabric into the column, or by winding the fabric around a hollow core pipe having pores, and passing the solution from the inside to the outside.

By packing the adsorbent according to the present invention into a column and by making a body fluid containing HMG proteins such as blood or plasma of a patient pass through the column by extracorporeal circulation, therapy of diseases such as sepsis may be carried out. By using the column according to the present invention together with a body fluid-purification column for adsorbing bacterial components, especially high therapeutic effect against sepsis is expected to be obtained. Further, the adsorbent of the present invention may also be suitably used for the therapy of diseases such as cancers and autoimmune diseases.

EXAMPLES

The present invention will now be described by way of examples thereof.

(Measuring Method)

(1) Rate of Adsorption of HMG-1

The HMG-1 concentrations of a sample before and after the reaction in each Example were determined by ELISA and the rate of adsorption was calculated in Example 4 according to the following equation:

Rate of Adsorption (%)={1−concentration after adsorption (ng/ml)/concentration before adsorption (ng/ml)}×100

In Examples 1-3, considering the increase in the volume of the solution by adding an adsorbent with high water content, the rate of adsorption was approximately calculated according to the following equation:

Rate of Adsorption (%)=[1−{concentration after adsorption (ng/ml)×0.45 (ml)}/{concentration before adsorption (ng/ml)×0.4 (ml)}]×100

(Note: 0.45=volume (ml) of reaction solution after adsorption, 0.4=volume (ml) of reaction solution before adsorption)

(2) Rate of Adsorption of Albumin

Serum albumin levels before and after the reaction were measured by using an automatic blood biochemistry analyzing apparatus (Fuji Drychem 5500 commercially available from Fuji Photo Film Co., Ltd), and the rate of adsorption of albumin was calculated in the same manner as in the calculation of rate of adsorption of HMG-1.

Example 1

Adsorption of HMG-1 by Beads Having Various Kinds of Functional Group

To normal human serum, bovine HMG-1 protein was added to a concentration of 600 ng/ml. To 0.4 ml of the obtained solution, 50 µl of crosslinked agarose beads containing one of the following types of functional groups were added, and each of the resulting solution was shaken at 37° C. for 2 hours.

Adsorbent: (1) $-N^+(CH_3)_3$, (2) $-N^+(C_2H_5)_2H$, (3) $-SO_3-$, (4) $-COO-$, (5) $-(CH_2)_7-CH_3$, (6) $-C_6H_5$ As a control, the solution to which the beads were not added was shaken for 2 hours in the same way. The results are shown in Table 1.

Among the water-insoluble carriers having these functional groups, those having cationic functional groups (1) and (2), and those having anionic functional groups (3) and (4) exhibited adsorption of HMG-1 with high efficiency. The hydrophobic functional groups (5) and (6) also showed adsorption. On the other hand, adsorption of albumin by these adsorbent was small.

TABLE 1

| Adsorbent | Rate of Adsorption of HMG-1(%) | Rate of Adsorption of Albumin (%) |
|---|---|---|
| Control | 0 | 0 |
| (1)-$N^+(CH_3)_3$ | 99 | 7 |
| (2)-$N^+(C_2H_5)_2H$ | 97 | 17 |
| (3)-$SO_3^-$ | 97 | 10 |
| (4)-$COO^-$ | 88 | 7 |
| (5)-$(CH_2)_7-CH_3$ | 51 | 15 |
| (6)-$C_6H_5$ | 69 | 17 |

Example 2

Adsorption by Physiologically Active Substance-Immobilized Beads

Using the crosslinked beads on which one of the various physiologically active substances shown in Table 2 was immobilized, the adsorption experiments of HMG-1 in normal human serum were carried out in the same manner as in Example 1. As shown in Table 2, the HMG-1 in the serum was adsorbed and removed with high efficiency by (2) heparin, (4) polyL-lysine, (5) dextran sulfate or (7) histamine, and adsorption of albumin which is necessary to the body was small.

Each adsorbent was prepared as follows: One gram of crosslinked agarose beads activated with cyanogen bromide were mixed with 10 ml of each physiologically active substance solution with a concentration of 5 mg/ml in 0.1 M aqueous sodium hydrogen carbonate solution containing 0.5 M sodium chloride, and the resulting mixture was allowed to react at 4° C. for 24 hours. Then ethanolamine was added to 0.1 M and the resulting mixture was allowed to react at room temperature for 2 hours, thereby blocking the non-reacted active groups. The obtained beads were washed with distilled water and used in the experiments.

TABLE 2

| Adsorbent | Rate of Adsorption of HMG-1 (%) | Rate of Adsorption of Albumin (%) |
|---|---|---|
| Control | 0 | 0 |
| (1) DNA-agarose | 39 | 13 |

TABLE 2-continued

| Adsorbent | Rate of Adsorption of HMG-1 (%) | Rate of Adsorption of Albumin (%) |
|---|---|---|
| (2) Heparin-agarose | 98 | 17 |
| (3) Polymixin B-agarose | 30 | 17 |
| (4) Poly-L-lysine-agarose | 97 | 17 |
| (5) Dextran sulfate | 91 | 13 |
| (6) Histamine-agarose | 72 | 10 |

Example 3

Adsorption by Amino Acid-Immobilized Beads

Using the crosslinked beads on which one of the various physiologically active substances shown in Table 2 was immobilized, the adsorption experiments of HMG-1 in normal human serum were carried out in the same manner as in Example 1. As shown in Table 3, (2) arginine-immobilized material showed high adsorption, and (1) lysine-immobilized material and (2) tryptophan-immobilzied material also showed adsorption. Adsorption of albumin by these materials was small.

Each adsorbent was prepared as follows: One gram of crosslinked agarose beads activated with cyanogen bromide were mixed with 10 ml of each amino acid solution with a concentration of 5 mg/ml in 0.1 M aqueous sodium hydrogen carbonate solution containing 0.5 M sodium chloride, and the resulting mixture was allowed to react at 4° C. for 24 hours. Then ethanolamine was added to 0.1 M and the resulting mixture was allowed to react at room temperature for 2 hours, thereby blocking the non-reacted active groups. The obtained beads were washed with distilled water and used in the experiments.

TABLE 3

| Adsorbent | Rate of Adsorption of HMG-1 (%) | Rate of Adsorption of Albumin (%) |
|---|---|---|
| Control | 0 | 0 |
| (1) L-lysine-agarose | 52 | 10 |
| (2) L-arginine-agarose | 83 | 13 |
| (3) L-phenylalanine-agarose | 31 | 13 |
| (4) L-tryptophan-agarose | 57 | 10 |

Example 4

Adsorption by Heparin-immobilized Fibrous Carrier

Sea-island type composite fibers (thickness: 2.6 denier, number of islands: 16) described in U.S. Pat. No. 4,661,260 consisting of 50 parts by weight of sea component (a mixture of 46 parts by weight of polystyrene and 4 parts by weight of polypropylene) and 50 parts by weight of island component (polypropylene) were mixed with 50 g of N-methyrol-α-chloroacetamide, 400 g of nitrobenzene, 400 g of 98% sulfuric acid and 0.85 g of paraformaldehyde, and the resulting mixture was allowed to react at 20° C. for 1 hour. The fibers were then washed with nitrobenzene and placed in water to stop the reaction. Thereafter, the fibers were again washed with methanol and warm water to obtain chloroacetamide-methylated crosslinked polystyrene fibers (hereinafter referred to as "AMPSt fibers" for short).

To 300 mg of AMPSt fibers, 8 ml of 1% v/v ethylenediamine solution in 0.1 M sodium hydrogen carbonate solution was added and the mixture was allowed to react at 37° C. for 3 hours, thereby introducing amino groups to the fibers. After washing the obtained aminated fibers, 6 ml of 6.7 mg/ml of aqueous heparin solution and 2 ml of 1-ethyl-3,3-dimethylaminopropylcarbodiimide hydrochloride solution were added and the resulting mixture was allowed to react at room temperature for 21 hours to obtain heparinated fibers. The obtained fibers will be hereinafter referred to as "Adsorbent A."

On the other hand, to 300 mg of AMPSt fibers, 8 ml of 1 mg/ml heparin-albumin conjugate preparation (SIGMA) solution in 0.1 M sodium hydrogen carbonate solution (pH 9.6) was added and the mixture was allowed to react at 37° C. for 16 hours. Then the fibers were reacted with Tris-HCl having a final concentration of 0.1 M so as to block the non-reacted active groups to obtain heparin-albumin-bound fibers. The obtained fibers will be hereinafter referred to as "Adsorbent B."

To normal human serum, bovine HMG-1 protein was added to a concentration of 600 ng/ml. To 0.4 ml of the obtained solution, 20 mg of Adsorbent A or Adsorbent B obtained by the method described above was added, and each mixture was allowed to react at 37° C. for 2 hours under shaking. The concentrations of HMG-1 and albumin in the serum before and after the reaction were measured and the results are shown in Table 4. It was shown that HMG-1 in the serum is adsorbed and removed by the fibers on which heparin is immobilized. The amount of albumin adsorbed by these materials was small.

TABLE 4

| Adsorbent | Rate of Adsorption of HMG-1 (%) | Rate of Adsorption of Albumin (%) |
|---|---|---|
| Control | 0 | 0 |
| (1) Adsorbent A | 61 | 15 |
| (2) Adsorbent B | 89 | 10 |

The invention claimed is:

1. A method for adsorbing high-mobility-group proteins in body fluid, comprising:
   contacting an adsorbent with body fluid so as to adsorb said high-mobility-group proteins in said body fluid to said adsorbent;
   wherein said adsorbent comprises a water-insoluble carrier on which a substance(s) having a hydrogen-bondable functional group(s) and/or a hydrophobic functional group is(are) immobilized, and
   wherein said adsorbent has a rate of adsorption for high-mobility-group proteins of not less than 50%, and has a rate of adsorption for serum albumin of not more than 20% and wherein said body fluid is blood.

2. The method according to claim 1, which is carried out by using a body fluid-purification column for removing high-mobility-group proteins, said body fluid-purification column comprising a column and said absorbent is packed in said column.

3. The method according to claim 1, wherein the body fluid is obtained from a patient that has sepsis.

4. The method according to claim 3, which is carried out by using a body fluid-purification column for removing high-mobility-group proteins, said body fluid- purification column comprising a column and said absorbent is packed in said column, together with a body fluid-purification column(s) which adsorbs a substance(s) originating from bacteria.

5. The method according to claim 2, wherein extracorporcal circulation of whole blood is attained by said body fluid-purification column step.

6. The method according to claim 1, wherein said hydrogen-bondable functional group(s) is(are) a cationic functional group(s).

7. The method according to claim 6, wherein said cationic functional group(s) is(are) at least one selected from the group consisting of a primary amino group, secondary amino group, tertiary amino group, imino group and/or quaternary ammonium group.

8. The method according to claim 6, wherein said cationic functional group(s) is(are) represented by the following formula (I):

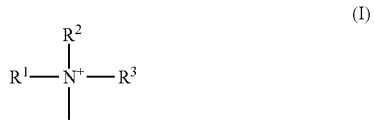

wherein each of $R^1$, $R^2$ and $R^3$ independently represents a hydrogen atom or a $C_1$-$C_5$ alkyl group.

9. The method according to claim 8, wherein each of $R^1$, $R^2$ and $R^3$ independently represents a hydrogen atom or a $C_1$-$C_2$ alkyl group.

10. The method according to claim 8, wherein each of $R^1$, $R^2$ and $R^3$ independently represents a methyl group.

11. The method according to claim 1, wherein said hydrogen-bondable functional group(s) is(are) an anionic functional group(s).

12. The method according to claim 11, wherein said hydrophobic functional group(s) is(are) at least one selected from the group consisting of a carboxyl group, sulfate group, sulfonic acid group and phosphate group.

13. The method according to claim 1, wherein said hydrophobic functional group(s) is(are) an alkyl group(s) having not less than 6 carbon atoms or an aromatic group(s).

14. The method according to claim 1, wherein said substance(s) having the hydrogen-bondable functional group(s) and/or a hydrophobic functional group(s) is(are) a peptide(s) or an amino acid(s).

15. The method according to claim 7, wherein said substance(s) having the hydrogen-bondable functional group(s) is(are) a peptide(s) or an amino acid(s) having an amino group(s) in its(their) side chain(s).

16. The method according, to claim 15, wherein said substance having the hydrogen-bondable functional group(s) is(are) polylysine.

17. The method according to claim 11, wherein a polysaccharide(s) having a sulfate group(s) is(are) immobilized.

18. The method according to claim 17, wherein said polysaccharide is heparin or dextran sulfate, or a derivative thereof.

19. The method according to claim 1, wherein said adsorbent comprises the water-insoluble carrier on which an antibody(ies) to said high-mobility-group proteins is(are) immobilized.

20. The method according to claim 19, wherein said adsorbent has a rate of adsorption for high-mobility-group proteins of not less than 50%, and has a rate of adsorption for serum albumin of not more than 20%.

21. The method according to claim 1 or 19, wherein said water-insoluble carrier is in the form of fibers.

22. The method according to claim 1 or 19, wherein said water-insoluble carrier is in the form of beads.

* * * * *